United States Patent
Nakazawa

(10) Patent No.: US 7,994,367 B2
(45) Date of Patent: Aug. 9, 2011

(54) METHOD FOR PRODUCING BENZALDEHYDE COMPOUND

(75) Inventor: Koichi Nakazawa, Toyonaka (JP)

(73) Assignee: Sumitomo Chemical Company, Limited, Tokyo (JP)

(*) Notice: Subject to any disclaimer, the term of this patent is extended or adjusted under 35 U.S.C. 154(b) by 0 days.

(21) Appl. No.: 12/599,041

(22) PCT Filed: May 14, 2008

(86) PCT No.: PCT/JP2008/059288
§ 371 (c)(1),
(2), (4) Date: Nov. 6, 2009

(87) PCT Pub. No.: WO2008/143264
PCT Pub. Date: Nov. 27, 2008

(65) Prior Publication Data
US 2010/0210879 A1    Aug. 19, 2010

(30) Foreign Application Priority Data
May 22, 2007 (JP) .................... 2007-135064

(51) Int. Cl.
C07C 45/61 (2006.01)
(52) U.S. Cl. ..................................... 568/437
(58) Field of Classification Search ............. 568/437
See application file for complete search history.

(56) References Cited

U.S. PATENT DOCUMENTS
5,145,980 A    9/1992  Wenderoth et al.

FOREIGN PATENT DOCUMENTS
JP        3017052 A     1/1991
JP        04029953 A    1/1992
JP        11279104 A    10/1999

OTHER PUBLICATIONS

Klis and J. Serwatowski, Halogen-Lithium exchange versus deprotonation: synthesis of diboronic acids derived from aryl-benzyl ethers, Tetrahedron Letters, vol. 48, No. 7, pp. 1169-1173, (2007).
Jikken Kagaku Kouza 15, Yuki Kagobutsu no Gosei III—Aldehyde Ketone, Quinone—, Edited by the Chemical Society of Japan, Maruzen Co., Ltd., 5th Edition pp. 81-84, (2003).

*Primary Examiner* — Sikarl Witherspoon
(74) *Attorney, Agent, or Firm* — Panitch Schwarze Belisario & Nadel LLP

(57) ABSTRACT

A method is provided for producing a benzaldehyde compound represented by the formula (4):

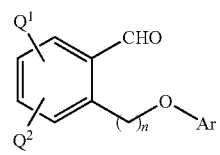

(4)

wherein $Q^1$ and $Q^2$ represent an alkyl group etc., n represents 1 or 2, and Ar represents a phenyl group etc., including the steps of reacting a compound represented by the formula (3):

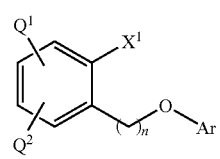

(3)

wherein $X^1$ represents a chlorine atom etc., and $Q^1$, $Q^2$, n and Ar are respectively the same meaning as above, with magnesium metal to obtain a Grignard compound and then reacting the obtained Grignard compound with a formylating agent.

11 Claims, No Drawings

METHOD FOR PRODUCING BENZALDEHYDE COMPOUND

CROSS-REFERENCE TO RELATED APPLICATION

This application is a section 371 of International Application No. PCT/JP2008/059288, filed May 14, 2008, which was published in the Japanese language on Nov. 27, 2008 under International Publication No. WO 2008/143264 A1 and the disclosure of which is incorporated herein by reference.

TECHNICAL FIELD

The present invention relates to a method for producing a benzaldehyde compound.

BACKGROUND ART

U.S. Pat. No. 5,145,980 discloses that benzaldehyde compounds having a phenoxymethyl group are useful as intermediates of bactericide and can be produced by reacting bromomethylbenzonitrile with a phenol compound followed by reducing the obtained mixture.

DISCLOSURE OF THE INVENTION

The present invention provides
<1> A method for producing a benzaldehyde compound represented by the formula (4):

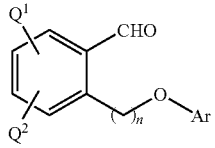

(4)

wherein $Q^1$ and $Q^2$ each independently represent a hydrogen atom; an alkyl group which may be substituted with at least one group selected from the group consisting of an alkoxy group, an alkylthio group, a phenylthio group, an alkanesulfonyl group which may be substituted with a fluorine atom, a benzenesulfonoyl group which may be substituted with a nitro group or an alkyl group, and a dialkylamino group which may be substituted with a phenyl group; an alkoxy group which may be substituted with at least one fluorine atom; an acyloxy group; an alkanesulfonyloxy group which may be substituted with at least one fluorine atom; a benzenesulfonyloxy group which may be substituted with at least one group selected from the group consisting of a nitro group and an alkyl group; a trialkylsilyloxy group; or an aryloxy group which may be substituted with at least one selected from the group consisting of an alkoxy group and a fluorine atom, n represents 1 or 2, and Ar represents a phenyl group which may be substituted with at least one selected from the group consisting of an alkyl group and a fluorine atom (hereinafter, simply referred to as the benzaldehyde compound (4)), comprising reacting a compound represented by the formula (3):

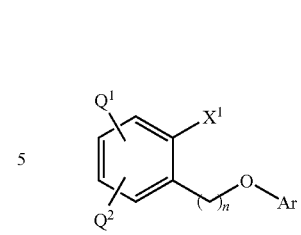

(3)

wherein $X^1$ represents a chlorine atom, a bromine atom or an iodine atom, and $Q^1$, $Q^2$, n and Ar are respectively the same meaning as above (hereinafter, simply referred to as the compound (3)), with magnesium metal to obtain a Grignard compound and then reacting the obtained Grignard compound with a formylating agent;
<2> The method according to the above <1>, wherein the reaction is conducted by adding a formylating agent to a Grignard compound;
<3> The method according to the above <1> or <2>, wherein the formylating agent is a N,N-dialkylformamide, a formic acid ester or a trialkoxymethane;
<4> The method according to the above <1> or <2>, wherein the formylating agent is a N,N-dialkylformamide;
<5> The method according to the above <3> or <4>, wherein the N,N-dialkylformamide is N,N-dimethylformamide;
<6> The method according to any of the above <1> to <5>, wherein n is 1;
<7> The method according to any of the above <1> to <6>, wherein Ar is a 2,5-dimethylphenyl group;
<8> The method according to any of the above <1> to <7>, wherein the compound represented by the formula (3) is one obtained by reacting a halobenzene compound represented by the formula (1):

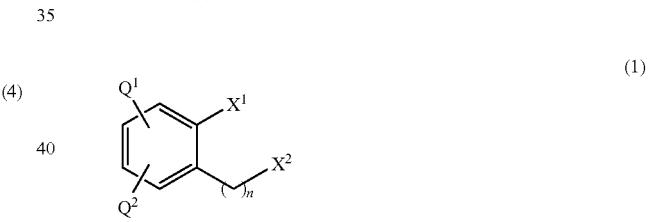

(1)

wherein $X^1$, $Q^1$, $Q^2$ and n are the same meaning as above and $X^2$ represents a fluorine atom, a chlorine atom, a bromine atom or an iodine atom (hereinafter, simply referred to as the halobenzene compound (1)), with a phenol compound represented by the formula (2):

Ar—OH     (2)

wherein Ar is the same as defined above (hereinafter, simply referred to as the phenol compound (2)), in the presence of a base;
<9> The method according to the above <8>, wherein the reaction is conducted by adding a halobenzene compound represented by the formula (1) to a mixture of a phenol compound represented by the formula (2) and a base;
<10> The method according to the above <8> or <9>, wherein the reaction of a halobenzene compound represented by the formula (1) and a phenol compound represented by the formula (2) is conducted in the presence of a phase transfer catalyst;
<11> The method according to the above <10>, wherein the phase transfer catalyst is a quaternary ammonium salt; and the like.

BEST MODE FOR CARRYING OUT THE PRESENT INVENTION

In the formula of the compound (3), $X^1$ represents a chlorine atom, a bromine atom or an iodine atom, and n represents 1 or 2.

$Q^1$ and $Q^2$ each independently represent a hydrogen atom; an alkyl group which may be substituted with at least one group selected from the group consisting of an alkoxy group, an alkylthio group, a phenylthio group, an alkanesulfonyl group which may be substituted with a fluorine atom, a benzenesulfonyl group which may be substituted with a nitro group or an alkyl group, and a dialkylamino group which may be substituted with a phenyl group; an alkoxy group which may be substituted with at least one fluorine atom; an acyloxy group; an alkanesulfonyloxy group which may be substituted with at least one fluorine atom; a benzenesulfonyloxy group which may be substituted with at least one group selected from the group consisting of a nitro group and an alkyl group; a trialkylsilyloxy group; or an aryloxy group which may be substituted with at least one selected from the group consisting of an alkoxy group and a fluorine atom.

Examples of the alkyl group include a C1-C6 alkyl group such as a methyl group, an ethyl group, a propyl group, an isopropyl group, a butyl group, an isobutyl group, a tert-butyl group, a pentyl group and a hexyl group.

Examples of the alkoxy group include a C1-C4 alkoxy group such as a methoxy group, an ethoxy group, a propoxy group and a butoxy group. Examples of the alkylthio group include a C1-C4 alkylthio group such as a methylthio group, an ethylthio group, a propylthio group and a butylthio group.

Examples of the alkanesulfonyl group which may be substituted with a fluorine atom include an unsubstituted C1-C4 alkanesulfonyl group such as a methanesulfonyl group and C1-C4 alkanesulfonyl group substituted with a fluorine atom such as a trifluoromethanesulfonyl group. Examples of the benzenesulfonyl group which may be substituted with a nitro group or an alkyl group include an unsubstituted benzenesulfonyl group, a benzenesulfonyl group substituted with a C1-C4 alkyl group such as a p-toluenesulfonyl group and a benzenesulfonyl group substituted with a nitro group such as an o-nitrobenzenesulfonyl group.

Examples of the dialkylamino group which may be substituted with a phenyl group include a dimethylamino group, a diethylamino group, a dipropylamino group, a diisopropylamino group, a benzylmethylamino group and a dibenzylamino group.

Specific examples of the alkyl group which may be substituted with at least one group selected from the group consisting of an alkoxy group, an alkylthio group, a phenylthio group, an alkanesulfonyl group which may be substituted with a fluorine atom, a benzenesulfonyl group which may be substituted with a nitro group or an alkyl group, and a dialkylamino group which may be substituted with a phenyl group include a methyl group, an ethyl group, a propyl group, an isopropyl group, a butyl group, an isobutyl group, a tert-butyl group, a pentyl group, a hexyl group, a methoxymethyl group, an ethoxymethyl group, a methylthiomethyl group, a phenylthiomethyl group, a methanesulfonylmethyl group, a trifluoromethanesulfonylmethyl group, a 4-benzenesulfonylmethyl group, 4-nitrobenzenesulfonylmethyl group, a dimethylaminomethyl group, a diethylaminomethyl group, a diisopropylaminomethyl group, a dibenzylaminomethyl group, a 2-methoxyethyl group, a 2-ethoxyethyl group, a 2-(methylthio)ethyl group, a 2-(phenylthio)ethyl group, a 2-methanesulfonylethyl group, a 2-trifluoromethanesulfonylethyl group, a 2-benzenesulfonylethyl group, a 2-(4-nitrobenzenesulfonylethyl) group, a 2-(dimethylamino)ethyl group, a 2-(diethylamino)ethyl group, a 2-(diisopropylamino)ethyl group and a 2-(dibenzylamino)ethyl group.

Examples of the alkoxy group which may be substituted with at least one fluorine atom include a C1-C4 alkoxy group such as a methoxy group, an ethoxy group, a propoxy group, an isopropoxy group and a butoxy group, and C1-C4 alkoxy group substituted with at least one fluorine atom such as a fluoromethoxy group, a difluoromethoxy group, a trifluoromethoxy group, a pentafluoroethoxy group and a 2-trifluoromethyl-3,3,3-trifluoropropoxy group.

Examples of the acyloxy group include a C2-C15 acyloxy group such as an acetoxy group, a propionyloxy group, a butyryloxy group, a pivaloyloxy group, a neopentanecarbonyloxy group, a benzoyloxy group, a naphthoyloxy group and a phenylacetoxy group.

Examples of the alkanesulfonyloxy group which may be substituted with at least one fluorine atom include an unsubstituted C1-C4 alkanesulfonyloxy group such as a methanesulfonyloxy group and an ethanesulfonyloxy group, and a C1-C4 alkanesulfonyloxy group substituted with at least one fluorine atom such as trifluoromethanesulfonyloxy group.

Examples of the benzenesulfonyloxy group which may be substituted with at least one group selected from the group consisting of a nitro group and an alkyl group include an unsubstituted benzenesulfonyloxy group, a benzenesulfonyloxy group substituted with a C1-C4 alkyl group such as a p-toluenesulfonyloxy group and a benzenesulfonyloxy group substituted with a nitro group such as an o-nitrobenzenesulfonyloxy group and a p-nitrobenzenesulfonyloxy group.

Examples of the trialkylsilyloxy group include a C3-C12 trialkylsilyloxy group such as a trimethylsilyloxy group, a triethylsilyloxy group, a tripropylsilyloxy group and a tert-butyldimethylsilyloxy group.

Examples of the aryloxy group which may be substituted with at least one selected from the group consisting of an alkoxy group and a fluorine atom include an unsubstituted C6-C20 aryloxy group such as a phenoxy group, a naphthyloxy group, a 4-methylphenoxy group, a 2-methylphenoxy group, a 2,4-dimethylphenoxy group and a 2,4-di-tert-butylphenoxy group, a C6-C20 aryloxy group substituted with a C1-C4 alkoxy group such as a 4-methoxyphenoxy group and a 4-ethoxyphenoxy group, and a C6-C20 aryl group substituted with at least one fluorine atom such as a 2-fluorophenoxy group, a 4-fluorophenoxy group and a pentafluorophenoxy group.

In the formula of the compound (3), Ar represents a phenyl group which may be substituted with at least one selected from the group consisting of a C1-C4 alkyl group and a fluorine atom.

Examples of the C1-C4 alkyl group include a methyl group, an ethyl group, a propyl group, an isopropyl group, a butyl group, an isobutyl group and a tert-butyl group.

Examples of Ar include a 2-methylphenyl group, a 4-methylphenyl group, a 5-methylphenyl group, a 2,5-dimethylphenyl group, a 2,4-dimethylphenyl group, a 2,6-dimethylphenyl group, a 2,4,6-trimethylphenyl group, a 2-ethylphenyl group, a 4-ethylphenyl group, a 5-ethylphenyl group, a 2,5-diethylphenyl group, a 2,4-diethylphenyl group, a 2,6-diethylphenyl group, a 2,4,6-triethylphenyl group, a 2-propylphenyl group, a 4-propylphenyl group, a 5-propylphenyl group, a 2,5-dipropylphenyl group, a 2,4-dipropylphenyl group, a 2,6-dipropylphenyl group, a 2,4,6-tripropylphenyl group, a 2-isopropylphenyl group, a 4-isopropylphenyl group, a 5-isopropylphenyl group, a 2,5-isopropylphenyl group, 2,4-diisopropylphenyl group, a 2,6-diisopropylphenyl group, a 2,4,6-triisopropylphenyl group, a 2-butylphenyl group, a 4-butylphenyl group, a 5-butylphenyl group, a 2,5-dibuylphenyl group, a 2,4-dibutylphenyl group, a 2,6-dibutylphenyl group, a 2,4,6-tribuylphenyl group, a 2-isobutylphenyl group, a 4-isobutylphenyl group, a 5-isobutylphenyl group, a 2,5-diisobutylphenyl group, a 2,4-diisobutylphenyl group, a 2,6-diisobutylphenyl group, a 2,4,6-triisobutylphenyl group, a 2-tert-butylphenyl group, a 4-tert-butylphenyl group, a 5-tert-butylphenyl group, a 2,5-di-tert-butylphenyl group, a 2,4-di-tert-butylphenyl group, a 2,6-di-tert-butylphenyl group, a 2,4,6-tri-tert-butylphenyl group, a 2-fluorophenyl group, a 4-fluorophenyl group, a 2,4-difluorophenyl group, a 2,4,6-trifluorophenyl group and a pentafluorophenyl group. Among them, a 2,5-dimethylphenyl group is preferable.

Examples of the compound (3) include 2-(phenoxymethyl)-1-bromobenzene, 2-(2-methylphenoxymethyl)-1-bromobenzene, 2-(4-methylphenoxymethyl)-1-bromobenzene, 2-(5-methylphenoxymethyl)-1-bromobenzene, 2-(2,5-dimethylphenoxymethyl)-1-bromobenzene, 2-(2,4-dimethylphenoxymethyl)-1-bromobenzene, 2-(2,6-dimethylphenoxymethyl)-1-bromobenzene, 2-(2,4,6-trimethylphenoxymethyl)-1-bromobenzene, 2-(2-ethylphenoxymethyl)-1-bromobenzene, 2-(4-ethylphenoxymethyl)-1-bromobenzene, 2-(5-ethylphenoxymethyl)-1-bromobenzene, 2-(2,5-diethylphenoxymethyl)-1-bromobenzene, 2-(2,4-diethylphenoxymethyl)-1-bromobenzene, 2-(2,6-diethylphenoxymethyl)-1-bromobenzene, 2-(2,4,6-triethylphenoxymethyl)-1-bromobenzene, 2-(2-propylphenoxymethyl)-1-bromobenzene, 2-(4-propylphenoxymethyl)-1-bromobenzene, 2-(5-propylphenoxymethyl)-1-bromobenzene, 2-(2,5-dipropylphenoxymethyl)-1-bromobenzene, 2-(2,4-dipropylphenoxymethyl)-1-bromobenzene, 2-(2,6-dipropylphenoxymethyl)-1-bromobenzene, 2-(2,4,6-tripropylphenoxymethyl)-1-bromobenzene, 2-(2-isopropylphenoxymethyl)-1-bromobenzene, 2-(4-isopropylphenoxymethyl)-1-bromobenzene, 2-(5-isopropylphenoxymethyl)-1-bromobenzene, 2-(2,5-isopropylphenoxymethyl)-1-bromobenzene, 2-(2,4-diisopropylphenoxymethyl)-1-bromobenzene, 2-(2,6-diisopropylphenoxymethyl)-1-bromobenzene, 2-(2,4,6-triisopropylphenoxymethyl)-1-bromobenzene, 2-(2-butylphenoxymethyl)-1-bromobenzene, 2-(4-butylphenoxymethyl)-1-bromobenzene, 2-(5-butylphenoxymethyl)-1-bromobenzene, 2-(2,5-dibutylphenoxymethyl)-1-bromobenzene, 2-(2,4-dibutylphenoxymethyl)-1-bromobenzene, 2-(2,6-dibutylphenoxymethyl)-1-bromobenzene, 2-(2,4,6-tributylphenoxymethyl)-1-bromobenzene, 2-(2-isobutylphenoxymethyl)-1-bromobenzene, 2-(4-isobutylphenoxymethyl)-1-bromobenzene, 2-(5-isobutylphenoxymethyl)-1-bromobenzene, 2-(2,5-diisobutylphenoxymethyl)-1-bromobenzene, 2-(2,4-diisobutylphenoxymethyl)-1-bromobenzene, 2-(2,6-diisobutylphenoxymethyl)-1-bromobenzene, 2-(2,4,6-triisobutylphenoxymethyl)-1-bromobenzene, 2-(2-tert-butylphenoxymethyl)-1-bromobenzene, 2-(4-tert-butylphenoxymethyl)-1-bromobenzene, 2-(5-tert-butylphenoxymethyl)-1-bromobenzene, 2-(2,5-di-tert-butylphenoxymethyl)-1-bromobenzene, 2-(2,4-di-tert-butylphenoxymethyl)-1-bromobenzene, 2-(2,6-di-tert-butylphenoxymethyl)-1-bromobenzene, 2-(2,4,6-tri-tert-butylphenoxymethyl)-1-bromobenzene, 2-(2-fluorophenoxymethyl)-1-bromobenzene, 2-(4-fluorophenoxymethyl)-1-bromobenzene, 2-(2,4-difluorophenoxymethyl)-1-bromobenzene, 2-(2,4,6-trifluorophenoxymethyl)-1-bromobenzene, 2-(pentafluorophenoxymethyl)-1-bromobenzene, 2-[2-(2,5-dimethylphenoxy)ethyl]-1-bromobenzene, 2-(2,6-dimethylphenoxymethyl)-4-tert-butyl-1-bromobenzene, 2-(2,6-dimethylphenoxymethyl)-4,6-dimethyl-1-bromobenzene, 2-(2,6-dimethylphenoxymethyl)-4,6-di-tert-butyl-1-bromobenzene, 2-(2,6-dimethylphenoxymethyl)-4-(methoxymethyl)-1-bromobenzene, 2-(2,6-dimethylphenoxymethyl)-4-(ethoxymethyl)-1-bromobenzene, 2-(2,6-dimethylphenoxymethyl)-4-(methylthiomethyl)-1-bromobenzene, 2-(2,6-dimethylphenoxymethyl)-4-(phenylthiomethyl)-1-bromobenzene, 2-(2,6-dimethylphenoxymethyl)-4-(methanesulfonylmethyl)-1-bromobenzene, 2-(2,6-dimethylphenoxymethyl)-4-(trifluoromethanesulfonylmethyl)-1-bromobenzene, 2-(2,6-dimethylphenoxymethyl)-4-(p-toluenesulfonylmethyl)-1-bromobenzene, 2-(2,6-dimethylphenoxymethyl)-4-(dimethylaminomethyl)-1-bromobenzene, 2-(2,6-dimethylphenoxymethyl)-4-(diethylaminomethyl)-1-bromobenzene, 2-(2,6-dimethylphenoxymethyl)-4-(diisopropylaminomethyl)-1-bromobenzene, 2-(2,6-dimethylphenoxymethyl)-4-methoxy-1-bromobenzene, 2-(2,6-dimethylphenoxymethyl)-4-ethoxy-1-bromobenzene, 2-(2,6-dimethylphenoxymethyl)-4-(trifluoromethoxy)-1-bromobenzene, 2-(2,6-dimethylphenoxymethyl)-4-(pentafluoroethoxy)-1-2-(2,6-dimethylphenoxymethyl)-4-(2-fluoromethyl-3,3,3-trifluoropropoxy)-1-bromobenzene, 2-(2,6-dimethylphenoxymethyl)-4,5-dimethoxy-1-bromobenzene, 2-(2,6-dimethylphenoxymethyl)-4-acetoxy-1-bromobenzene, 2-(2,6-dimethylphenoxymethyl)-4-benzoyloxy-1-bromobenzene, 2-(2,6-dimethylphenoxymethyl)-4-(phenylacetoxy)-1-bromobenzene, 2-(2,6-dimethylphenoxymethyl)-4,5-diacetoxy-1-bromobenzene, 2-(2,6-dimethylphenoxymethyl)-4,5-dibenzoyloxy-1-bromobenzene, 2-(2,6-dimethylphenoxymethyl)-4,5-bis(phenylacetoxy)-1-bromobenzene, 2-(2,6-dimethylphenoxymethyl)-4-(methanesulfonyloxy)-1-bromobenzene, 2-(2,6-dimethylphenoxymethyl)-4-(trifluoromethanesulfonyloxy)-1-bromobenzene, 2-(2,6-dimethylphenoxymethyl)-4,5-bis(methanesulfonyloxy)-1-bromobenzene, 2-(2,6-dimethylphenoxymethyl)-4,5-bis(trifluoromethanesulfonyloxy)-1-bromobenzene, 2-(2,6-dimethylphenoxymethyl)-4-(p-toluenesulfonyloxy)-1-bromobenzene, 2-(2,6-dimethylphenoxymethyl)-4-(p-nitrobenzenesulfonyloxy)-1-bromobenzene, 2-(2,6-dimethylphenoxymethyl)-4,5-bis(p-toluenesulfonyloxy)-1-bromobenzene, 2-(2,6-dimethylphenoxymethyl)-4,5-bis(p-nitrobenzenesulfonyloxy)-1-bromobenzene, 2-(2,6-dimethylphenoxymethyl)-4-(trimethylsilyloxy)-1-bromobenzene, 2-(2,6-dimethylphenoxymethyl)-4-(triethylsilyloxy)-1-bromobenzene, 2-(2,6-dimethylphenoxymethyl)-4-(tert-butyldimethylsilyloxy)-1-bromobenzene, 2-(2,6-dimethylphenoxymethyl)-4,5-bis(trimethylsilyloxy)-1-bromobenzene, 2-(2,6-dimethylphenoxymethyl)-4,5-bis(triethylsilyloxy)-1-bromobenzene, 2-(2,6-dimethylphenoxymethyl)-4,5-bis(tert-butyldimethylsilyloxy)-1-bromobenzene, 2-(2,6-dimethylphenoxymethyl)-4-phenoxy-1-bromobenzene, 2-(2,6-dimethylphenoxymethyl)-4-(2-methylphenoxy)-1-bromobenzene, 2-(2,6-dimethylphenoxymethyl)-4-(2,4-dimethylphenoxy)-1-bromobenzene, 2-(2,6-dimethylphenoxymethyl)-4-(2,4-di-tert-butylphenoxy)-1-bromobenzene, 2-(2,6-dimethylphenoxymethyl)-4-(4-methoxyphenoxy)-1-bromobenzene, 2-(2,6-dimethylphenoxymethyl)-4-(2-fluorophenoxy)-1- bromobenzene, 2-(2,6-dimethylphenoxymethyl)-4-(4-fluorophenoxy)-1-bromobenzene, 2-(2,6-dimethylphenoxymethyl)-4-pentafluorophenoxy-1-bromobenzene, 2-(2,6-dimethylphenoxymethyl)-4-methyl-6-ethyl-1-bromobenzene, 2-(2,6-dimethylphenoxymethyl)-4-methoxy-6-methyl-1-bromobenzene, 2-(2,6-dimethylphenoxymethyl)-4-(dimethylaminomethyl)-6-methyl-1-bromobenzene, 2-(2,6-dimethylphenoxymethyl)-4-acetoxy-6-methyl-1-bromobenzene, 2-(2,6-dimethylphenoxymethyl)-4-methanesulfonyloxy-6-methyl-1-bromobenzene, 2-(2,6-dimethylphenoxymethyl)-4-(p-toluenesulfonyloxy)-6-methyl-1-bromobenzene, 2-(2,6-dimethylphenoxymethyl)-4-trimethylsilyloxy-6-methyl-1-bromobenzene, 2-(2,6-dimethylphenoxymethyl)-4-methoxymethyl-6-tert-butyl-1-bromobenzene, 2-(2,6-dimethylphenoxymethyl)-4-acetoxy-6-tert-butyl-1-bromobenzene, 2-(2,6-dimethylphenoxymethyl)-4-methanesulfonyloxy-6-tert-butyl-1-bromobenzene, 2-(2,6-dimethylphenoxymethyl)-4-(p-toluenesulfonyloxy)-6-tert-butyl-1-bromobenzene and 2-(2,6-dimethylphenoxymethyl)-4-trimethylsilyloxy-6-tert-butyl-1-bromobenzene.

As magnesium metal, commercially available one is usually used. The used amount thereof is usually 0.9 mole or more and preferably 1 to 3 moles per 1 mole of the halobenzene compound (3).

The reaction may be conducted in the presence of additives in order that the reaction of the halobenzene compound (3) and magnesium metal may proceed more smoothly.

Examples of the additives include halogens and halides. Examples of halogens include iodine, and examples of halides include a C1-C2 alkyl halide such as methyl iodide, ethyl iodide, 1,2-dibromoethane and 1,2-diiodoethane, a C1-C3 alkyl magnesium halide such as methyl magnesium bromide, methyl magnesium iodide, ethyl magnesium bromide, ethyl magnesium iodide, propyl magnesium bromide and propyl magnesium iodide, and a C6-C10 aryl magnesium halide such as phenyl magnesium bromide and phenyl magnesium iodide.

As additives, commercially available one may be used as it is. When a C1-C3 alkyl magnesium halide or a C6-C10 aryl magnesium halide is used as additives, one produced according to known methods such as a method comprising reacting magnesium metal with the corresponding alkyl halide or aryl halide (e.g. "Shin Jikken Kagaku Koza 12 Yukikinzokukagaku" Fourth Chapter (1976), edited by Chemical Society of Japan, issued by Maruzen Co., Ltd.).

The used amount of additives is usually 0.01 mole or more and preferably 0.03 to 0.5 mole per 1 mole of the halobenzene compound (3).

The reaction of the halobenzene compound (3) and magnesium metal is usually carried out in the presence of a solvent. Examples of the solvent include aromatic hydrocarbon solvents such as xylene, toluene and benzene, aliphatic hydrocarbon solvents such as pentane, hexane, heptane and cyclohexane, and ether solvents such as tetrahydrofuran, diethyl ether, tert-butyl methyl ether and cyclopentyl methyl ether. The solvent may be used alone and two or more kinds thereof may be mixed to be used. Among them, a mixed solvent of the ether solvent and the aromatic hydrocarbon solvent is preferable and a mixed solvent of tetrahydrofuran and toluene is more preferable.

While the used amount of the solvent is not particularly limited, it is usually 100 parts by weight or less per 1 part by weight of the halobenzene compound (3) from the viewpoint of economic efficiency.

The temperature of the reaction of the halobenzene compound (3) and magnesium metal is usually −40° C. or more and a boiling point of the solvent or less, and preferably 10 to 50° C. The reaction may be conducted under a normal pressure and under pressure.

The progress of the reaction can be checked by a conventional analytical means such as gas chromatography, high performance liquid chromatography and NMR.

The reaction of the halobenzene compound (3) and magnesium metal is carried out by mixing the halobenzene compound (3) with magnesium metal in the solvent. While the mixing order is not particularly limited, the halobenzene compound (3) is preferably added to a mixture of magnesium metal and the solvent.

The obtainable mixture includes a Grignard compound represented by the following formula:

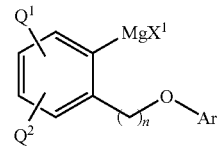

wherein $X^1$, $Q^1$, $Q^2$, Ar and n respectively represent the same meanings as defined above, and the obtained reaction mixture containing the Grignard compound may be used for a reaction with a formylating agent as it is, after diluting with a solvent or after concentrating.

Examples of the formylating agent include N,N-dialkylformamides such as N,N-dimethylformamide and N,N-diethylformamide, formic acid esters such as methyl formic acid ester, ethyl formic acid ester and phenyl formic acid ester and trialkoxymethanes such as methyl orthoformate, and N,N-dialkylformamides are preferable and N,N-dimethylformamide is more preferable.

The used amount of the formylating agent may be usually 0.9 mole or more per 1 mole of the Grignard compound. While there is no specific upper limit thereof, it is preferably 1 to 3 moles.

The reaction of the Grignard compound and the formylating agent is usually conducted in the presence of a solvent. Examples of the solvent include the same as those of the reaction of the halobenzene compound (3) and magnesium metal. While the used amount of the solvent is not particularly limited, it is usually 100 parts by weight or less per 1 part by weight of the Grignard compound from the viewpoint of economic efficiency.

The temperature of the reaction of the Grignard compound and the formylating agent is usually −40° C. or more and the boiling point of the solvent or less, and preferably 10 to 50° C. The reaction may be conducted under a normal pressure and under pressure.

The progress of the reaction can be checked by a conventional analytical means such as gas chromatography, high performance liquid chromatography and NMR.

The reaction of the Grignard compound and the formylating agent is usually carried out by mixing the Grignard compound with the formylating agent. While the reaction may be conducted by adding the Grignard compound to the formylating agent and by adding the formylating agent to the Grignard compound, the reaction is preferably conducted by adding the formylating agent to the Grignard compound.

The benzaldehyde compound (4) can be isolated, for example, by concentrating the obtained reaction mixture, if necessary, after washing it with an acid or water. The isolated benzaldehyde compound (4) may be further purified by a conventional purification means such as recrystallization, distillation and column chromatography.

Examples of the benzaldehyde compound (4) include 2-(4-methylphenoxymethyl)benzaldehyde, 2-(phenoxymethyl) benzaldehyde, 2-(2-methylphenoxymethyl)benzaldehyde, 2-(4-methylphenoxymethyl)benzaldehyde, 2-(5-methylphenoxymethyl)benzaldehyde, 2-(2,5-dimethylphenoxymethyl) benzaldehyde, 2-(2,4-dimethylphenoxymethyl)benzaldehyde, 2-(2,6-dimethylphenoxymethyl)benzaldehyde, 2-(2,4,6-trimethylphenoxymethyl)benzaldehyde, 2-(2-ethylphenoxymethyl)benzaldehyde, 2-(4-ethylphenoxymethyl)benzaldehyde, 2-(5-ethylphenoxymethyl)benzaldehyde, 2-(2,5-diethylphenoxymethyl)benzaldehyde, 2-(2,4-diethylphenoxymethyl)benzaldehyde, 2-(2,6-diethylphenoxymethyl)benzaldehyde, 2-(2,4,6-triethylphenoxymethyl)benzaldehyde, 2-(2-propylphenoxymethyl)benzaldehyde, 2-(4-propylphenoxymethyl)benzaldehyde, 2-(5-propylphenoxymethyl)benzaldehyde, 2-(2,5-dipropylphenoxymethyl)benzaldehyde, 2-(2,4-dipropylphenoxymethyl)benzaldehyde, 2-(2,6-dipropylphenoxymethyl)benzaldehyde, 2-(2,4,6-tripropylphenoxymethyl)benzaldehyde, 2-(2-isopropylphenoxymethyl)benzaldehyde, 2-(4-isopropylphenoxymethyl)benzaldehyde, 2-(5-isopropylphenoxymethyl)benzaldehyde, 2-(2,5-isopropylphenoxymethyl)benzaldehyde, 2-(2,4-diisopropylphenoxymethyl)benzaldehyde, 2-(2,6-diisopropylphenoxymethyl)benzaldehyde, 2-(2,4,6-triisopropylphenoxymethyl)benzaldehyde, 2-(2-butylphenoxymethyl)benzaldehyde, 2-(4-butylphenoxymethyl)benzaldehyde, 2-(5-butylphenoxymethyl)benzaldehyde, 2-(2,5-dibutylphenoxymethyl)benzaldehyde, 2-(2,4-dibutylphenoxymethyl)benzaldehyde, 2-(2,6-dibutylphenoxymethyl)benzaldehyde, 2-(2,4,6-tributylphenoxymethyl)benzaldehyde, 2-(2-isobutylphenoxymethyl)benzaldehyde, 2-(4-isobutylphenoxymethyl)benzaldehyde, 2-(5-isobutylphenoxymethyl)benzaldehyde, 2-(2,5-diisobutylphenoxymethyl)benzaldehyde, 2-(2,4-diisobutylphenoxymethyl)benzaldehyde, 2-(2,6-diisobutylphenoxymethyl)benzaldehyde, 2-(2,4,6-triisobutylphenoxymethyl)benzaldehyde, 2-(2-tert-butylphenoxymethyl)benzaldehyde, 2-(4-tert-butylphenoxymethyl)benzaldehyde, 2-(5-tert-butylphenoxymethyl)benzaldehyde, 2-(2,5-di-tert-butylphenoxymethyl)benzaldehyde, 2-(2,4-di-tert-butylphenoxymethyl)benzaldehyde, 2-(2,6-di-tert-butylphenoxymethyl)benzaldehyde, 2-(2,4,6-tri-tert-butylphenoxymethyl)benzaldehyde, 2-(2-fluorophenoxymethyl)benzaldehyde, 2-(4-fluorophenoxymethyl)benzaldehyde, 2-(2,4-difluorophenoxymethyl)benzaldehyde, 2-(2,4,6-trifluorophenoxymethyl)benzaldehyde, 2-pentafluorophenoxymethylbenzaldehyde, 2-[2-(2,5-dimethylphenoxyethyl)]benzaldehyde, 2-(2,6-dimethylphenoxymethyl)-4-tert-butylbenzaldehyde, 2-(2,6-dimethylphenoxymethyl)-4,6-dimethylbenzaldehyde, 2-(2,6-dimethylphenoxymethyl)-4,6-di-tert-butylbenzaldehyde, 2-(2,6-dimethylphenoxymethyl)-4-(methoxymethyl)benzaldehyde, 2-(2,6-dimethylphenoxymethyl)-4-(ethoxymethyl)benzaldehyde, 2-(2,6-dimethylphenoxymethyl)-4-(methylthiomethyl)benzaldehyde, 2-(2,6-dimethylphenoxymethyl)-4-(phenylthiomethyl) benzaldehyde, 2-(2,6-dimethylphenoxymethyl)-4-(methanesulfonylmethyl)benzaldehyde, 2-(2,6-dimethylphenoxymethyl)-4-(trifluoromethanesulfonylmethyl)benzaldehyde, 2-(2,6-dimethylphenoxymethyl)-4-(p-toluenesulfonylmethyl) benzaldehyde, 2-(2,6-dimethylphenoxymethyl)-4-(dimethylaminomethyl)benzaldehyde, 2-(2,6-dimethylphenoxymethyl)-4-(diethylaminomethyl) benzaldehyde, 2-(2,6-dimethylphenoxymethyl)-4-(diisopropylaminomethyl)benzaldehyde, 2-(2,6-dimethylphenoxymethyl)-4-methoxybenzaldehyde, 2-(2,6-dimethylphenoxymethyl)-4-ethoxybenzaldehyde, 2-(2,6-dimethylphenoxymethyl)-4-trifluoromethoxybenzaldehyde, 2-(2,6-dimethylphenoxymethyl)-4-pentafluoroethoxybenzaldehyde, 2-(2,6-dimethylphenoxymethyl)-4-(2-fluoromethyl-3,3,3-trifluoropropoxy)benzaldehyde, 2-(2,6-dimethylphenoxymethyl)-4,5-dimethoxybenzaldehyde, 2-(2,6-dimethylphenoxymethyl)-4-acetoxybenzaldehyde, 2-(2,6-dimethylphenoxymethyl)-4-benzoyloxybenzaldehyde, 2-(2,6-dimethylphenoxymethyl)-4-(phenylacetoxy) benzaldehyde, 2-(2,6-dimethylphenoxymethyl)-4,5-diacetoxybenzaldehyde, 2-(2,6-dimethylphenoxymethyl)-4,5-dibenzoyloxybenzaldehyde, 2-(2,6-dimethylphenoxymethyl)-4,5-bis(phenylacetoxy) benzaldehyde, 2-(2,6-dimethylphenoxymethyl)-4-(methanesulfonyloxy)benzaldehyde, 2-(2,6-dimethylphenoxymethyl)-4-(trifluoromethanesulfonyloxy) benzaldehyde, 2-(2,6-dimethylphenoxymethyl)-4,5-bis(methanesulfonyloxy)benzaldehyde, 2-(2,6-dimethylphenoxymethyl)-4,5-bis (trifluoromethanesulfonyloxy)benzaldehyde, 2-(2,6-dimethylphenoxymethyl)-4-(p-toluenesulfonyloxy) benzaldehyde, 2-(2,6-dimethylphenoxymethyl)-4-(p-nitrobenzenesulfonyloxy)benzaldehyde, 2-(2,6-dimethylphenoxymethyl)-4,5-bis(p-toluenesulfonyloxy) benzaldehyde, 2-(2,6-dimethylphenoxymethyl)-4,5-bis(p-nitrobenzenesulfonyloxy)benzaldehyde, 2-(2,6-dimethylphenoxymethyl)-4-(trimethylsilyloxy) benzaldehyde, 2-(2,6-dimethylphenoxymethyl)-4-(triethylsilyloxy)benzaldehyde, 2-(2,6-dimethylphenoxymethyl)-4-(tert-butyldimethylsilyloxy) benzaldehyde, 2-(2,6-dimethylphenoxymethyl)-4,5-bis (trimethylsilyloxy)benzaldehyde, 2-(2,6-dimethylphenoxymethyl)-4,5-bis(triethylsilyloxy) benzaldehyde, 2-(2,6-dimethylphenoxymethyl)-4,5-bis(tert-butyldimethylsilyloxy)benzaldehyde, 2-(2,6-dimethylphenoxymethyl)-4-phenoxybenzaldehyde, 2-(2,6-dimethylphenoxymethyl)-4-(2-methylphenoxy) benzaldehyde, 2-(2,6-dimethylphenoxymethyl)-4-(2,4-dimethylphenoxy)benzaldehyde, 2-(2,6-dimethylphenoxymethyl)-4-(2,4-di-tert-butylphenoxy) benzaldehyde, 2-(2,6-dimethylphenoxymethyl)-4-(4-methoxyphenoxy)benzaldehyde, 2-(2,6-dimethylphenoxymethyl)-4-(2-fluorophenoxy) benzaldehyde, 2-(2,6-dimethylphenoxymethyl)-4-(4-fluorophenoxy)benzaldehyde, 2-(2,6-dimethylphenoxymethyl)-4-pentafluorophenoxybenzaldehyde, 2-(2,6-dimethylphenoxymethyl)-4-methyl-6-ethylbenzaldehyde, 2-(2,6-dimethylphenoxymethyl)-4-methoxy-6-methylbenzaldehyde, 2-(2,6-dimethylphenoxymethyl)-4-(dimethylaminomethyl)-6-methylbenzaldehyde, 2-(2,6-dimethylphenoxymethyl)-4-acetoxy-6-methylbenzaldehyde, 2-(2,6-dimethylphenoxymethyl)-4-methanesulfonyloxy-6-methylbenzaldehyde, 2-(2,6-dimethylphenoxymethyl)-4-(p-toluenesulfonyloxy)-6-methylbenzaldehyde, 2-(2,6-dimethylphenoxymethyl)-4-trimethylsilyloxy-6- methylbenzaldehyde, 2-(2,6-dimethylphenoxymethyl)-4-(methoxymethyl)-6-tert-butylbenzaldehyde, 2-(2,6-dimethylphenoxymethyl)-4-acetoxy-6-tert-butylbenzaldehyde, 2-(2,6-dimethylphenoxymethyl)-4-methanesulfonyloxy-6-tert-butylbenzaldehyde, 2-(2,6-dimethylphenoxymethyl)-4-(p-toluenesulfonyloxy)-6-tert-butylbenzaldehyde and 2-(2,6-dimethylphenoxymethyl)-4-trimethylsilyloxy-6-tert-butylbenzaldehyde.

The compound (3) can be produced by reacting the halobenzene compound (1) with the phenol compound (2) in the presence of a base.

In the formula of the halobenzene compound (1), X2 represents a fluorine atom, a chlorine atom, a bromine atom or an iodine atom.

Examples of the halobenzene compound (1) include 2-(fluoromethyl)-1-chlorobenzene, 2-(fluoromethyl)-1-bromobenzene, 2-(fluoromethyl)-1-iodobenzene, 2-2-(chloromethyl)-1-bromobenzene, 2-(chloromethyl)-1-iodobenzene, 2-(bromomethyl)-1-chlorobenzene, 2-(bromomethyl)-1-bromobenzene, 2-(bromomethyl)-1-iodobenzene, 2-(iodomethyl)-1-chlorobenzene, 2-(iodomethyl)-1-bromobenzene, 2-2-(2-chloroethyl)-1-chlorobenzene, 2-(2-bromoethyl)-1-bromobenzene, 4-methyl-2-(bromomethyl)-1-bromobenzene, 4-isopropyl-2-(bromomethyl)-1-bromobenzene, 4-butyl-2-(bromomethyl)-1-bromobenzene, 4,6-dimethyl-2-(bromomethyl)-1-bromobenzene, 4,6-di-tert-butyl-2-(bromomethyl)-1-bromobenzene, 4-methoxymethyl-2-(bromomethyl)-1-bromobenzene, 4-ethoxymethyl-2-(bromomethyl)-1-bromobenzene, 4-(methylthiomethyl)-2-(bromomethyl)-1-bromobenzene, 4-(phenylthiomethyl)-2-(bromomethyl)-1-bromobenzene, 4-methanesulfonylmethyl-2-(bromomethyl)-1-bromobenzene, 4-trifluoromethanesulfonylmethyl-2-(bromomethyl)-1-bromobenzene, 4-(p-toluenesulfonylmethyl)-2-(bromomethyl)-1-bromobenzene, 4-(dimethylaminomethyl)-2-(bromomethyl)-1-bromobenzene, 4-(diisopropylaminomethyl)-2-(bromomethyl)-1-bromobenzene, 4-methoxy-2-(bromomethyl)-1-bromobenzene, 4-ethoxy-2-(bromomethyl)-1-bromobenzene, 4-trifluoromethoxy-2-(bromomethyl)-1-bromobenzene, 4-pentafluoroethoxy-2-(bromomethyl)-1-bromobenzene, 2-bromomethyl-4-(2-trifluoromethyl-3,3,3-trifluoropropoxy)-1-bromobenzene, 4,5-dimethoxy-2-(bromomethyl)-1-bromobenzene, 4-acetoxy-2-(bromomethyl)-1-bromobenzene, 4-benzoyloxy-2-(bromomethyl)-1-bromobenzene, 4,5-diacetoxy-2-(bromomethyl)-1-bromobenzene, 4,5-dibenzoyloxy-2-(bromomethyl)-1-bromobenzene, 4-methanesulfonyloxy-2-(bromomethyl)-1-bromobenzene, 4-trifluoromethanesulfonyloxy-2-(bromomethyl)-1-bromobenzene, 4,5-bis(methanesulfonyloxy)-2-(bromomethyl)-1-bromobenzene, 2-bromomethyl-4,5-bis(trifluoromethanesulfonyloxy)-1-bromobenzene, 2-bromomethyl-4-(p-toluenesulfonyloxy)-1-bromobenzene, 2-bromomethyl-4-(p-nitrobenzenesulfonyloxy)-1-bromobenzene, 2-bromomethyl-4,5-bis(p-toluenesulfonyloxy)-1-bromobenzene, 2-bromomethyl-4,5-bis(p-nitrobenzenesulfonyloxy)-1-bromobenzene, 4-trimethylsilyloxy-2-(bromomethyl)-1-bromobenzene, 4-triethylsilyloxy-2-(bromomethyl)-1-bromobenzene, 4-tert-butyldimethylsilyloxy-2-(bromomethyl)-1-bromobenzene, 4,5-bis(trimethylsilyloxy)-2-(bromomethyl)-1-bromobenzene, 4,5-bis(triethylsilyloxy)-2-(bromomethyl)-1-bromobenzene, 4,5-bis(tert-butyldimethylsilyloxy)-2-(bromomethyl)-1-bromobenzene, 4-phenoxy-2-(bromomethyl)-1-bromobenzene, 2-(bromomethyl)-4-(2-methylphenoxy)-1-bromobenzene, 2-(bromomethyl)-4-(2,4-dimethylphenoxy)-1-bromobenzene, 2-(bromomethyl)-4-(2,4-di-tert-butylphenoxy)-1-bromobenzene, 2-(bromomethyl)-4-(4-methoxyphenoxy)-1-bromobenzene, 2-(bromomethyl)-4-(2-fluorophenoxy)-1-bromobenzene, 2-(bromomethyl)-4-(4-fluorophenoxy)-1-bromobenzene, 2-(bromomethyl)-4-(pentafluorophenoxy)-1-bromobenzene, 4-methyl-6-ethyl-2-(bromomethyl)-1-bromobenzene, 4-methoxy-6-methyl-2-(bromomethyl)-1-bromobenzene, 4-(dimethylaminomethyl)-6-methyl-2-(bromomethyl)-1-bromobenzene, 4-acetoxy-6-methyl-2-(bromomethyl)-1-bromobenzene, 2-(bromomethyl)-4-methanesulfonyloxy-6-methyl-1-bromobenzene, 2-(bromomethyl)-4-(p-toluenesulfonyloxy)-6-methyl-1-bromobenzene, 2-bromomethyl-4-trimethylsilyloxy-6-methyl-1-bromobenzene, 2-bromomethyl-4-methoxymethyl-6-tert-butyl-1-bromobenzene, 2-bromomethyl-4-acetoxy-6-tert-butyl-1-bromobenzene, 2-bromomethyl-4-methanesulfonyloxy-6-tert-butyl-1-bromobenzene, 2-bromomethyl-4-(p-toluenesulfonyloxy)-6-tert-butyl-1-bromobenzene and 2-bromomethyl-4-trimethylsilyloxy-6-tert-butyl-1-bromobenzene.

As the halobenzene compound (1), commercially available one may be used and one produced according to known methods described in Synlett, 18, 2837 (2005), Syn. Comm., 11, 669 (1981) or the like may be used.

Examples of the phenol compound (2) include 2-methylphenol, 4-methylphenol, 5-methylphenol, 2,5-dimethylphenol, 2,4-dimethylphenol, 2,6-dimethylphenol, 2,4,6-trimethylphenol, 2-ethylphenol, 4-ethylphenol, 5-ethylphenol, 2,5-diethylphenol, 2,4-diethylphenol, 2,6-diethylphenol, 2,4,6-triethylphenol, 2-propylphenol, 4-propylphenol, 5-propylphenol, 2,5-dipropylphenol, 2,4-dipropylphenol, 2,6-dipropylphenol, 2,4,6-tripropylphenol, 2-isoproylphenol, 4-isoproylphenol, 5-isoproylphenol, 2,5-isoproylphenol, 2,4-diisoproylphenol, 2,6-diisoproylphenol, 2,4,6-triisoproylphenol, 2-butylphenol, 4-butylphenol, 5-butylphenol, 2,5-dibutylphenol, 2,4-dibutylphenol, 2,6-dibutylphenol, 2,4,6-tributylphenol, 2-isobutylphenol, 4-isobutylphenol, 5-isobutylphenol, 2,5-diisobutylphenol, 2,4-diisobutylphenol, 2,6-diisobutylphenol, 2,4,6-triisobutylphenol, 2-tert-butylphenol, 4-tert-butylphenol, 5-tert-butylphenol, 2,5-di-tert-butylphenol, 2,4-di-tert-butylphenol, 2,6-di-tert-butylphenol, 2,4,6-tri-tert-butylphenol, 2-fluorophenol, 4-fluorophenol, 2,4-difluorophenol, 2,4,6-trifluorophenol and pentafluorophenol. Among them, 2,5-dimethylphenol is preferable.

As the phenol compound (2), commercially available one may be used and one produced according to known methods described in J. Am. Chem. Soc., 128, 10694 (2006), Tetrahedron Letters, 30, 5215 (1989), JP 2002-3426 A or the like may be used.

While 10 moles or more of the phenol compound (2) may be used per 1 mole of the halobenzene compound (1) and 10 moles or more of the halobenzene compound (1) may be used per 1 mole of the phenol compound (2), 0.1 to 10 moles of the phenol compound (2) is preferably used and 1 to 3 moles of the phenol compound (2) is more preferably used per 1 mole of the halobenzene compound (1).

Examples of the base include tertiary amines such as trimethylamine, triethylamine and diisopropylethylamine, metal alkoxides such as sodium methoxide, sodium ethoxide and potassium tert-butoxide, alkali metal hydroxides such as lithium hydroxide, sodium hydroxide and potassium hydroxide, alkali metal hydrides such as sodium hydride, potassium hydride and lithium hydride, alkali metal carbonates such as sodium carbonate, potassium carbonate and lithium carbonate, and alkali metal hydrogen carbonates such as sodium hydrogen carbonate, potassium hydrogen carbonate and lithium hydrogen carbonate. The used amount thereof is usually 1 mole or more and preferably 1 to 3 moles per 1 mole of one of which used amount is lower among the halobenzene compound (1) and the phenol compound (2).

The reaction of the halobenzene compound (1) and the phenol compound (2) is usually conducted in the presence of a solvent. Examples of the solvent include aromatic hydrocarbon solvents such as xylene, toluene and benzene, aliphatic hydrocarbon solvents such as pentane, hexane, heptane and cyclohexane, ether solvents such as tetrahydrofuran, diethyl ether, tert-butyl methyl ether and cyclopentyl methyl ether, and water. These solvents may be used alone and two or more may be mixed to be used. A mixed solvent of water and an aromatic hydrocarbon solvent is preferable and a mixed solvent of water and toluene is more preferable. While the used amount of the solvent is not particularly limited, it is usually 100 parts by weight or less per 1 part by weight of the halobenzene compound (1) from the viewpoint of economic efficiency.

The reaction of the halobenzene compound (1) and the phenol compound (2) is preferably conducted in the presence of a phase transfer catalyst. Examples of the phase transfer catalyst include quaternary ammonium salts such as tetra-n-butylammonium bromide, benzyltriethylammonium chloride, tetra-n-butylammonium hydrogen sulfate and trioctylmethylammonium chloride, phosphonium salts such as triphenylphosphine bromide, and polyether compounds such as 19-crown-6 and polyethylene glycol. Among them, quaternary ammonium salts are preferable and tetra-n-butylammonium bromide is more preferable. The used amount of the phase transfer catalyst is usually 0.01 mole or more and preferably 0.05 to 1 mole per 1 mole of one of which used amount is lower among the halobenzene compound (1) and the phenol compound (2).

The reaction may be carried out in the presence of an iodine compound in order that the reaction of the halobenzene compound (1) and the phenol compound (2) may proceed smoothly. Examples of the iodine compound include alkali metal iodides such as potassium iodide, sodium iodide and lithium iodide, and iodine. As the iodine compound, commercially available one is usually used as it is. The used amount of the iodine compound is usually 0.01 mole or more per 1 mole of one of which used amount is lower among the halobenzene compound (1) and the phenol compound (2), and there is no specific upper limit. It is preferably 0.05 to 1 mole.

The reaction temperature is usually –5° C. or more, and the boiling point of the solvent or less. It is preferably 10 to 100° C. The reaction may be carried out under a normal pressure and under pressure.

The progress of the reaction can be checked by a conventional analytical means such as gas chromatography, high performance liquid chromatography and NMR.

The reaction is conducted by mixing the halobenzene compound (1), the phenol compound (2) and the base. While the mixing order thereof is not particularly limited, the halobenzene compound (1) is preferably added to a mixture of the phenol compound (2) and the base.

The obtained reaction mixture containing the halobenzene compound (3) may be used as it is for the reaction with metal magnesium. Additionally, the reaction mixture is neutralized and if necessary, a water-insoluble organic solvent is added thereto to conduct an extraction, and the obtained organic layer containing the halobenzene compound (3) may be used for the reaction with metal magnesium. The organic layer is concentrated to isolate the halobenzene compound (3) and it may be used.

EXAMPLES

The present invention will be illustrated in more detail by Examples below. The present invention is not limited to these Examples. The analysis was conducted by high performance liquid chromatography internal standard method.

Example 1

(1) Into a 1000 mL round-bottomed flask, 25.7 g of 2,5-dimethylphenol and 200 mL of toluene were charged. To the obtained solution, 3.2 g of tetra-n-butylammonium bromide was added at room temperature, and 22.0 g of 40% by weight aqueous sodium hydroxide solution was further added dropwise thereto. The obtained mixture was stirred at 90° C. for 2 hours. The obtained mixture was cooled to 60° C. and a mixed solution of 50.0 g of 2-bromomethylbromobenzene and 50 mL of toluene was added dropwise thereto over 2 hours while keeping at 60° C. The obtained mixture was stirred at the same temperature for 3 hours. The obtained reaction mixture was cooled to room temperature and 125.0 g of 15% by weight aqueous sodium hydroxide solution was added thereto to stir. The obtained mixture was left and then, separated to an organic layer and an aqueous layer. The organic layer was washed twice with 125.0 g of 10% by weight aqueous sodium hydroxide solution, and then, was washed with 75.0 g of water. The obtained organic layer was concentrated under reduced pressure to remove a part of toluene and water to obtain 131.0 g of a solution containing 2-(2,5-dimethylphenoxymethyl)bromobenzene. Content: 40.0% by weight. Yield: 90.0% (based on 2-bromomethylbromobenzene).

(2) Into a 500 mL round-bottomed flask, 5.0 g of magnesium metal and 5.7 mL of tetrahydrofuran were charged. The obtained mixture was adjusted at 35° C., and 13.1 g of the solution containing 2-(2,5-dimethylphenoxymethyl)bromobenzene, which was obtained in the above-mentioned (1), was added dropwise thereto over 15 minutes. It was confirmed that the inner temperature had increased to 40° C. by adding. A mixed solution of 117.9 g of the solution containing 2-(2,5-dimethylphenoxymethyl)bromobenzene, which was obtained in the above-mentioned (1), and 36.7 g of tetrahydrofuran was added dropwise thereto over 5 hours while keeping at an inner temperature of 40° C. After completion of the addition, stirring was conducted at the same temperature for 3 hours. The obtained mixture was cooled to room temperature and 52.5 g of a toluene solution of N,N-dimethylformamide (content: 50.1% by weight) was added dropwise thereto over 1 hour. The obtained mixture was stirred at room temperature for 1 hour to obtain a reaction mixture.

Into a 500 mL round-bottomed flask, 132.4 g of 20% by weight aqueous sulfuric acid solution was charged, and the reaction mixture obtained above was added dropwise thereto over 1 hour while keeping at an inner temperature of 25° C. Further, pH of an aqueous layer in the obtained mixture was adjusted to 5.0 by adding 10.0 g of 20% by weight aqueous sulfuric acid solution thereto. The mixture was left and then separated to an organic layer and an aqueous layer. The organic layer was washed with 104.8 g of water, and then, was washed with 104.8 g of 5% by weight aqueous sodium hydroxide solution. The obtained organic layer was concentrated under reduced pressure to remove a part of toluene and water to obtain 159.4 g of a solution containing 2-(2,5-dimethylphenoxymethyl)benzaldehyde. Content: 24.8% by weight.

Yield: 91.4% (based on 2-(2,5-dimethylphenoxymethyl)bromobenzene).

Example 2

(1) Into a 300 mL round-bottomed flask, 13.5 g of 2,5-dimethylphenol and 120 mL of toluene were charged. To the obtained solution, 1.62 g of tetra-n-butylammonium bromide was added at room temperature, and 10.5 g of 40% by weight aqueous sodium hydroxide solution was further added dropwise thereto. The obtained mixture was stirred at 90° C. for 2 hours. The obtained mixture was cooled to 60° C. and a mixed solution of 25.1 g of 2-bromomethylbromobenzene and 30 mL of toluene was added dropwise thereto over 2 hours while keeping at an inner temperature of 60° C. The obtained mixture was stirred at the same temperature for 3 hours.

The obtained reaction mixture was cooled to room temperature and 37.6 g of 15% by weight aqueous sodium hydroxide solution was added thereto to stir. The obtained mixture was left and then, separated to an organic layer and an aqueous layer. The organic layer was washed twice with 50.0 g of 10% by weight aqueous sodium hydroxide solution, and then, was washed with 37.6 g of water. The obtained organic layer was concentrated under reduced pressure to remove a part of toluene and water to obtain 85.1 g of a solution containing 2-(2,5-dimethylphenoxymethyl)bromobenzene. Content: 31.7% by weight. Yield: 92.5% (based on 2-bromomethylbromobenzene).

(2) Into a 100 mL round-bottomed flask, 1.2 g of magnesium metal and 5.0 mL of tetrahydrofuran were charged. The obtained mixture was adjusted at 35° C., and 4.0 g of a toluene solution of 2-(2,5-dimethylphenoxymethyl)bromobenzene (content: 29.1% by weight) was added dropwise thereto over 15 minutes. It was confirmed that the inner temperature had increased to 40° C. by adding. A mixed solution of 36.0 g of a toluene solution of 2-(2,5-dimethylphenoxymethyl)bromobenzene (content: 30.6% by weight) and 8.6 g of tetrahydrofuran was added dropwise thereto over 5 hours while keeping at an inner temperature of 40° C. The obtained mixture was stirred at the same temperature for 3 hours. The obtained mixture was cooled to room temperature and 12.2 g of a toluene solution of N,N-dimethylformamide (content: 50.1% by weight) was added dropwise thereto over 1 hour. The obtained mixture was stirred at room temperature for 1 hour to obtain a reaction mixture.

Into a 200 mL round-bottomed flask, 30.9 g of 20% by weight aqueous sulfuric acid solution was charged, and the reaction mixture obtained above was added dropwise thereto over 1 hour while keeping at an inner temperature of 25° C. Further, pH of an aqueous layer in the obtained mixture was adjusted to 4.8 by adding 3.0 g of 20% by weight aqueous sulfuric acid solution thereto. The mixture was separated to an organic layer and an aqueous layer. The organic layer was washed with 24.5 g of water, and then, was washed with 24.5 g of 5% by weight aqueous sodium hydroxide solution. The obtained organic layer was concentrated under reduced pressure to remove a part of toluene and water to obtain 39.5 g of a solution containing 2-(2,5-dimethylphenoxymethyl)benzaldehyde. Content: 25.0% by weight.
Yield: 92.0% (based on 2-(2,5-dimethylphenoxymethyl)bromobenzene).

Example 3

(1) Into a 30 mL round-bottomed flask, 180 mg of magnesium metal and 0.5 mL of tetrahydrofuran were charged. The obtained mixture was adjusted at 35° C., and 0.6 g of a toluene solution of 2-(2,5-dimethylphenoxymethyl)bromobenzene (content: 32.7% by weight) was added dropwise thereto over 15 minutes. It was confirmed that the inner temperature had increased to 40° C. by adding. A mixed solution of 5.4 g of a toluene solution of 2-(2,5-dimethylphenoxymethyl)bromobenzene (content: 32.7% by weight) and 1.0 g of tetrahydrofuran was added dropwise thereto over 5 hours while keeping at an inner temperature of 40° C. The obtained mixture was stirred at the same temperature for 3 hours. The obtained mixture was cooled to room temperature and 2.0 g of a toluene solution of N,N-dimethylformamide (content: 50.1% by weight), which was adjusted at 0° C., was added dropwise thereto over 1 hour. The obtained mixture was stirred at room temperature for 1 hour to obtain a reaction mixture.

Into a 30 mL round-bottomed flask, 10.8 g of 10% by weight aqueous sulfuric acid solution was charged, and the reaction mixture obtained above was added dropwise thereto over 1 hour while keeping at an inner temperature of 25° C. Further, pH of an aqueous layer in the obtained mixture was adjusted to 4.8 by adding 0.3 g of 20% by weight aqueous sulfuric acid solution thereto. The mixture was separated to an organic layer and an aqueous layer. The obtained organic layer was washed with 10.8 g of water, and then, was concentrated under reduced pressure to remove toluene and water to obtain 1.72 g of a solution containing 2-(2,5-dimethylphenoxymethyl)benzaldehyde. Content: 78.5% by weight.
Yield: 83.3% (based on 2-(2,5-dimethylphenoxymethyl)bromobenzene).

INDUSTRIAL APPLICABILITY

According to the present invention, a benzaldehyde compound, which is useful as an intermediate of bactericide, can be obtained.

The invention claimed is:

1. A method for producing a benzaldehyde compound represented by the formula (4):

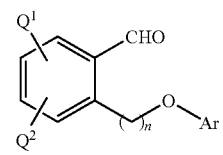

(4)

wherein $Q^1$ and $Q^2$ each independently represent a hydrogen atom; an alkyl group which may be substituted with at least one group selected from the group consisting of an alkoxy group, an alkylthio group, a phenylthio group, an alkanesulfonyl group which may be substituted with a fluorine atom, a benzenesulfonyl group which may be substituted with a nitro group or an alkyl group, and a dialkylamino group which may be substituted with a phenyl group; an alkoxy group which may be substituted with at least one fluorine atom; an acyloxy group; an alkanesulfonyloxy group which may be substituted with at least one fluorine atom; a benzenesulfonyloxy group which may be substituted with at least one group selected from the group consisting of a nitro group and an alkyl group; a trialkylsilyloxy group; or an aryloxy group which may be substituted with at least one selected from the group consisting of an alkoxy group and a fluorine atom, n represents 1 or 2, and Ar represents a phenyl group which may be substituted with at least one selected from the group consisting of an alkyl group and a fluorine atom, comprising reacting a compound represented by the formula (3):

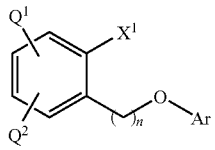
(3)

wherein $X^1$ represents a chlorine atom, a bromine atom or an iodine atom, and $Q^1$, $Q^2$, n and Ar are respectively the same meaning as above, with magnesium metal to obtain a Grignard compound and then reacting the obtained Grignard compound with a formylating agent.

2. The method according to claim 1, wherein the reaction is conducted by adding a formylating agent to a Grignard compound.

3. The method according to claim 1, wherein the formylating agent is a N,N-dialkylformamide, a formic acid ester or a trialkoxymethane.

4. The method according to claim 1, wherein the formylating agent is a N,N-dialkylformamide.

5. The method according to claim 4, wherein the N,N-dialkylformamide N,N-dimethylformamide.

6. The method according to claim 1, wherein n is 1.

7. The method according to claim 1, wherein Ar is a 2,5-dimethylphenyl group.

8. The method according to claim 1, wherein the compound represented by the formula (3) is one obtained by reacting a halobenzene compound represented by the formula (1):

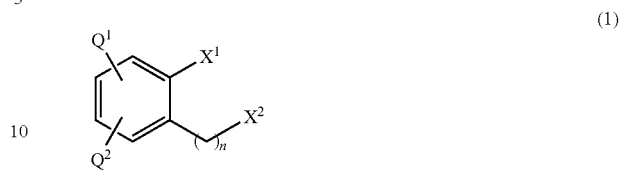
(1)

wherein $X^1$, $Q^1$, $Q^2$ and n are the same meaning as above and $X^2$ represents a fluorine atom, a chlorine atom, a bromine atom or an iodine atom, with a phenol compound represented by the formula (2):

Ar—OH  (2)

wherein Ar is the same as defined above, in the presence of a base.

9. The method according to claim 8, wherein the reaction is conducted by adding a halobenzene compound represented by the formula (1) to a mixture of a phenol compound represented by the formula (2) and a base.

10. The method according to claim 8, wherein the reaction of a halobenzene compound represented by the formula (1) and a phenol compound represented by the formula (2) is conducted in the presence of a phase transfer catalyst.

11. The method according to claim 10, wherein the phase transfer catalyst is a quaternary ammonium salt.

* * * * *